United States Patent
Gargione

(10) Patent No.: US 6,613,024 B1
(45) Date of Patent: Sep. 2, 2003

(54) SINGLE HAND CONTROLLED DOSAGE SYRINGE

(76) Inventor: Frank V. Gargione, 106 S. Genoa Ave., Egg Harbor, NJ (US) 08215

( * ) Notice: Subject to any disclaimer, the term of this patent is extended or adjusted under 35 U.S.C. 154(b) by 0 days.

(21) Appl. No.: 10/173,507

(22) Filed: Jun. 18, 2002

(51) Int. Cl.⁷ .......................... A61M 5/315; A61M 5/00
(52) U.S. Cl. ...................... 604/218; 604/220; 604/235
(58) Field of Search .................. 604/218, 220, 604/235, 187, 110, 15, 87

(56) References Cited

U.S. PATENT DOCUMENTS

| | | | | |
|---|---|---|---|---|
| 1,039,591 A | | 9/1912 | Prideaux | 604/187 |
| 2,688,965 A | * | 9/1954 | Huber | |
| 4,664,128 A | | 5/1987 | Lee | 604/187 |
| 4,693,706 A | * | 9/1987 | Ennis, III | 604/87 |
| 5,078,690 A | | 1/1992 | Ryan | 604/187 |
| 5,147,303 A | * | 9/1992 | Martin | 604/110 |
| 5,681,292 A | * | 10/1997 | Tober et al. | 604/195 |
| 5,957,897 A | * | 9/1999 | Jeffrey | 604/223 |
| 5,984,897 A | * | 11/1999 | Petersen et al. | 604/187 |
| 5,997,512 A | * | 12/1999 | Shaw | 604/195 |
| 6,221,055 B1 | * | 4/2001 | Shaw et al. | 604/232 |

* cited by examiner

*Primary Examiner*—Sharon Kennedy
(74) *Attorney, Agent, or Firm*—Brady, O'Boyle & Gates

(57) ABSTRACT

A single-hand controlled syringe having a plunger slidably mounted within a barrel. The plunger and barrel are of double wall construction with the outer wall of the plunger being slidably mounted in the space between the inner and outer walls of the barrel. A spring is mounted in the space between the inner and outer walls of the plunger. By this construction and arrangement, the alignment of the plunger within the barrel is maintained; the spring is hidden from view and the syringe can be easily assembled and disassembled for cleaning.

8 Claims, 2 Drawing Sheets

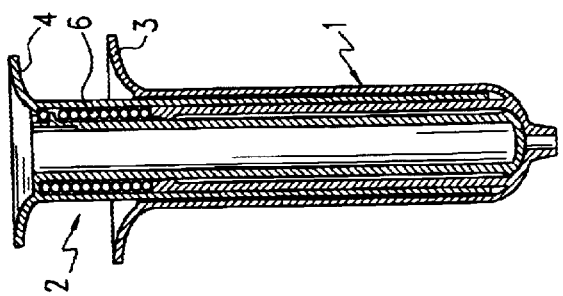
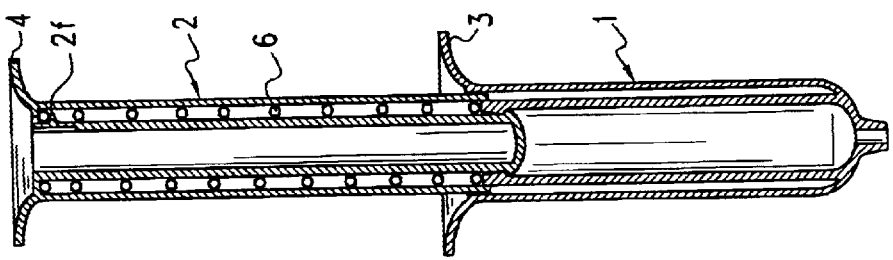
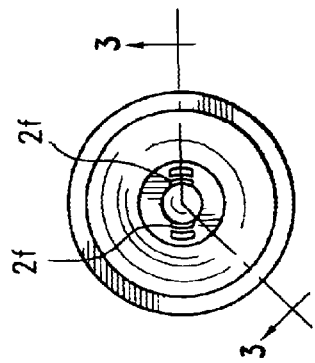
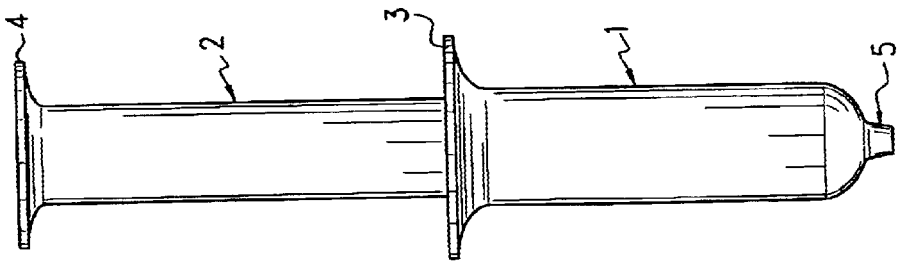

SINGLE HAND CONTROLLED DOSAGE SYRINGE

BACKGROUND OF THE INVENTION

Various single-hand controlled dosage syringes have been proposed wherein a spring biased plunger is slidably mounted within a barrel. Suitable grips are provided on the barrel and plunger so that the palm of the hand of a user can be placed on the barrel grip and the fingers of the same hand can be placed on the plunger grip, whereby the plunger can be pushed into the barrel to dispense a dosage therefrom.

While these single-hand controlled dosage syringes have been satisfactory for their intended purpose, they have been characterized by a complicated construction and a misalignment of the plunger within the barrel resulting in a difficult manipulation of the syringe to dispense a dosage.

The appearance of the prior art single-hand controlled dosage syringes could also be traumatic to a child being fed or injected with a dosage.

SUMMARY OF THE INVENTION

To overcome the disadvantages experienced with prior art single-hand controlled dosage syringes, the single-hand dosage controlled dosage syringe of the present invention has been devised which comprises, essentially, a barrel having a double wall open at one end thereof and a plunger having a double wall open at one end thereof. The plunger is slidably mounted in the barrel with the outer wall of the plunger slidably mounted in the space between the inner and outer walls of the plunger and is biased between the end of the inner wall of the barrel and the closed end of the plunger double wall.

By this construction and arrangement, the alignment of the plunger within the barrel is maintained and the spring is hidden from view.

The plunger and barrel can also be disassembled for cleaning purposes.

BRIEF DESCRIPTION OF THE DRAWINGS

FIG. 1 is a side elevational view of the singlehand controlled dosage syringe of the present invention;

FIG. 2 is a top plan view of the syringe shown in FIG. 1;

FIG. 3 is a view taken along line 3—3 of FIG. 2;

FIG. 4 is a sectional side elevational view showing the plunger fully telescoped within the barrel; and, FIG. 5 is an enlarged, fragmentary, sectional, side elevational view of the syringe of the present invention.

DESCRIPTION OF THE PREFERRED EMBODIMENT

Figure 5:
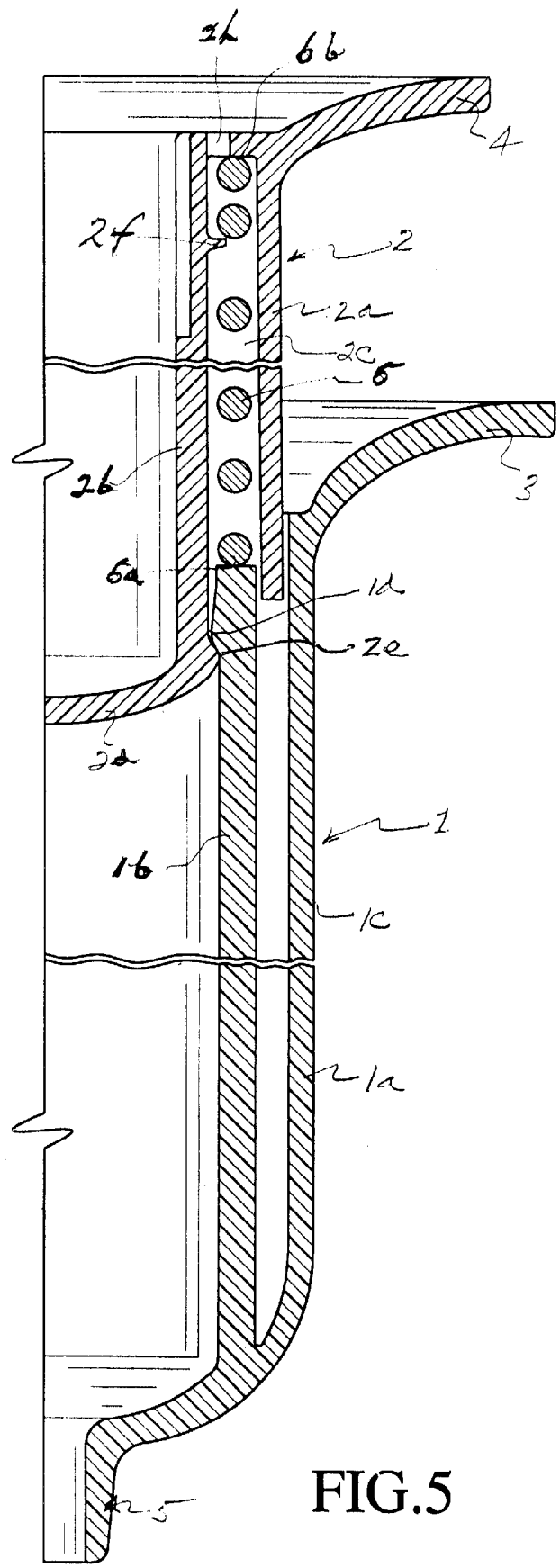

Referring to the drawings and more particularly to FIG. 1, the single-hand controlled dosage syringe of the present invention comprises a barrel 1 having a plunger 2 slidably mounted therein. The corresponding ends of the barrel and plunger are provided with respective hand grips 3 and 4; and a discharge opening 5 of the barrel 1 can be provided with a press-in bottle adapter, as shown, or a conventional luer connector for a hypodermic needle, not shown.

The details of the construction of the syringe are illustrated in FIG. 5 wherein it will be seen that the barrel 1 is of a double wall construction having an outer wall $1a$ spaced radially outwardly from an inner wall $1b$, to thereby provide a space $1c$ therebetween.

The plunger 2 is of a similar double wall construction having an outer wall $2a$ spaced radially outwardly from an inner wall $2b$, to thereby provide a space $2c$ therebetween. The outer wall $2a$ of the plunger 2 is slidably mounted in the space $1c$ between the outer and inner walls $1a$, $1b$ of the barrel 1 to facilitate the alignment of the plunger 2 within the barrel.

A coil spring 6 is positioned in the space $2c$ between the outer and inner walls $2a$, $2b$ of the plunger 2. One end of the spring 6 engages the end of the inner wall of the barrel as at $6a$, and the opposite end of the spring 6 engages the closed end of the space $2c$ as at $6b$. By this construction and arrangement, the spring 6 is enclosed within the plunger space $2c$; thus being hidden from view.

The closed end $2d$ of the plunger 2 is provided with a protrusion $2e$ which sealingly engages the inner surface of the barrel inner wall $1b$. While a sealing engagement is shown between the plunger protrusion $2e$ and inner surface of the barrel inner wall $1b$, a seal could also be obtained by mounting a seal member; such as an O-ring, on the plunger for engaging the barrel wall. The upper end portion of the barrel inner wall $1b$ is provided with a shoulder portion $1d$ which is adapted to engage the protrusion $2e$ on the plunger 2 to thereby provide a stop to limit the outward travel of the plunger 2 from the barrel 1.

Flexible fingers $2f$ extend radially outwardly from the inner wall $2b$ of the plunger 2 and engage a turn of the coil spring 6 for retaining the coil spring within the plunger space $2c$.

To complete the structural description of the syringe of the present invention, a drain hole $2h$ is provided in the end wall of the plunger space $2c$ for draining cleaning fluid from the syringe after the cleansing thereof.

To assemble the syringe of the present invention, the coil spring 6 is inserted into the plunger space $2c$ and snapped over the fingers $2f$. The plunger 2 and associated coil spring 6 are inserted into the barrel 1 with the plunger outer wall $2a$ being positioned within the barrel space $1c$. The inner wall $1b$ of the barrel 1 is flexible thus allowing the plunger protrusion portion $2e$ to cam over the barrel shoulder portion $1d$.

In use, the thumb of the hand of a user can be placed on the plunger grip 4 and the fingers of the same hand can be placed on the barrel grip 3. By moving the thumb of the hand on the plunger grip 4 toward the fingers of the barrel grip 3, the plunger 2 is pushed into the barrel 1 against the biasing force of the spring 6 to expel a dosage from the barrel 1 as shown in FIG. 4. When released, the plunger 2 is biased outwardly from the barrel 1 as shown in FIG. 3.

To fill the syringe with a desired dosage of fluid, the plunger 2 of an empty syringe is telescoped into the barrel 1 against the biasing force of the spring 6, as shown in FIG. 4. The discharge opening 5 is inserted into a supply container and the thumb of the user is gradually released from the plunger grip 4 allowing the spring to expand in a controlled manner to bias the plunger 2 outwardly of the barrel 1, as shown in FIG. 3, whereby a measured dosage of fluid is drawn into the barrel. It will be understood by those skilled in the art that dosage indicia can be placed on either the plunger or barrel side walls so that the outward movement of the plunger can be controlled to obtain the desired dosage in the barrel; and when the outer wall $1a$ of the barrel 1 is transparent, the bottom edge of the outer wall $2a$ of the plunger 2 functions as a dosage indicator.

To clean the syringe, the plunger 2 can be pulled outwardly of the barrel to override the stop function between the barrel shoulder portion 1d and the plunger protrusion portion 2e. The plunger fingers 2f will retain the spring 6 within the plunger space 2c. The components can then be washed and the syringe re-assembled as noted above.

From the description, it will be appreciated by those skilled in the art that the single-hand controlled dosage syringe of the present invention is an improvement over hitherto employed syringes in that the construction is simple so that it can be easily assembled and disassembled for cleaning. The construction and arrangement of the cooperating spaced inner and outer walls of the barrel 1 and plunger 2 facilitates the alignment of the plunger 2 within the barrel 1, and by positioning the coil spring 6 within the plunger space 2c, the spring is hidden from, view, thus providing a more pleasing appearance.

It is understood that the form of the invention herewith shown and described is to be taken as a preferred example of the same, and that various changes in the shape, size, material and arrangement of parts may be resorted to, without departing from, the spirit of the invention or scope of the subjoined claims.

I claim:

1. A single-hand controlled dosage syringe comprising a barrel, a plunger, slidably mounted within said barrel, hand grips provided on corresponding end portions of the barrel and plunger, a discharge opening at an end portion of the barrel, the barrel having a double wall provided by an outer wall spaced radially outwardly from an inner wall, to thereby provide a space therebetween, the plunger having a double wall provided by an outer wall spaced radially outwardly from an inner wall, to thereby provide a space therebetween, the outer wall of the plunger being slidably mounted in the space between the outer and inner walls of the barrel to thereby facilitate the alignment of the plunger within the barrel, a spring interposed the plunger and barrel for biasing the plunger outwardly of the barrel, said spring being mounted in the space between the outer and inner walls of the plunger, whereby the spring is hidden from view.

2. A single-hand controlled dosage syringe according to claim 1 wherein the spring is a coil spring, said spring having one end engaging an end portion of the inner wall of the barrel, the opposite end of said spring engaging a closed end of the space between the inner and outer walls of the plunger.

3. A single-hand controlled dosage syringe according to claim 2, wherein a finger extends radially outwardly from the inner wall of said plunger, said finger engaging a turn on the coil spring for retaining the coil spring in said space.

4. A single-hand controlled dosage syringe according to claim 3, wherein a drain hole is provided in said closed end.

5. A single-hand controlled dosage syringe according to claim 1, wherein a seal is provided between the outer surface of the inner wall of the plunger and the inner surface of the inner wall of the barrel.

6. A single-hand controlled dosage syringe according to claim 5, wherein the seal comprises a protrusion on the plunger.

7. A single-hand controlled dosage syringe according to claim 6, wherein a shoulder portion is provided on the upper end portion of the barrel inner wall, said shoulder portion adapted to engage the protrusion on the plunger to thereby provide a stop to limit the outward travel of the plunger from the barrel.

8. A single-hand controlled dosage syringe according to claim 7, wherein the inner wall of said barrel is flexible thus facilitating the assembly and disassembly of the syringe.

* * * * *